United States Patent [19]

Hayden et al.

[11] Patent Number: 4,507,508

[45] Date of Patent: Mar. 26, 1985

[54] PROCESS FOR THE PRODUCTION OF UNSATURATED MONO- OR SATURATED DIALDEHYDES AND ACETALS THEREOF

[75] Inventors: Percy Hayden; Alec Mee; Donald Wright, all of Cleveland, England

[73] Assignee: Imperial Chemical Industries PLC, London, England

[21] Appl. No.: 490,510

[22] Filed: May 2, 1983

[30] Foreign Application Priority Data

May 11, 1982 [GB] United Kingdom ............... 8213650
Feb. 2, 1983 [GB] United Kingdom ............... 8302884

[51] Int. Cl.$^3$ ............................................. C07C 45/49
[52] U.S. Cl. .................................... 568/487; 568/485; 568/494
[58] Field of Search ............... 568/452, 454, 487, 471, 568/494, 485, 448

[56] References Cited

U.S. PATENT DOCUMENTS

| | | | |
|---|---|---|---|
| 3,168,553 | 2/1965 | Slaugh | 568/487 |
| 3,752,859 | 8/1973 | Schell | 568/487 |
| 4,101,588 | 7/1978 | Nienburg et al. | 568/487 |
| 4,224,236 | 9/1980 | Wunder et al. | 518/714 |
| 4,224,239 | 9/1980 | Tashiro et al. | 562/401 |

FOREIGN PATENT DOCUMENTS 1455645 11/1976 United Kingdom ............... 568/494

OTHER PUBLICATIONS

Fell et al., "Tetrahedron Letters", No. 32, pp. 2721–2723, (1969), Pergamon Press (Britain).

Primary Examiner—Werren B. Lone
Attorney, Agent, or Firm—Cushman, Darby & Cushman

[57] ABSTRACT

Unsaturated mono- and saturated di-aldehydes and acetals are produced by reacting a conjugated diolefine with carbon monoxide and hydrogen in the presence of an alcohol and a catalyst comprising rhodium, a tert phosphine or phosphite and more than one equivalent of acid per gram atom of rhodium.

10 Claims, No Drawings

PROCESS FOR THE PRODUCTION OF UNSATURATED MONO- OR SATURATED DIALDEHYDES AND ACETALS THEREOF

It is known from British Patent Specification No. 1,455,645 that dialdehydes and acetals thereof may be produced by reacting a conjugated diene with an alcohol, carbon monoxide and hydrogen in the presence of a catalyst which is a rhodium complex which contains carbon monoxide, a tertiary organic phosphine or a tertiary organic phosphite and a halogen atom.

We have found that an improvement may be obtained by the presence of acid in excess of one equivalent per gram atom of rhodium, and that the halogen atom is unnecessary when such excess acid is present. The acid may be added as such or as a substance which produces the acid in situ, for example, in part from the rhodium complex.

This invention comprises a process in which an unsaturated mono- or a saturated di-aldehyde or acetal thereof is produced by reacting a conjugated diolefine having 4 to 6 carbon atoms, for example isoprene, or preferably butadiene, with carbon monoxide, hydrogen and an alcohol in the presence of a catalyst which comprises rhodium and a tertiary phosphine or phosphite, acid being present in excess of one equivalent per gram atom of rhodium.

Preferably the catalyst is substantially free from halogen.

The catalyat may be supplied as a preformed complex or as its components; for example the rhodium may be supplied as a metal, an oxide or a salt for example rhodium acetate. The phosphine or phosphite and acid may be supplied as such.

Suitably rhodium is present in a concentration of 5 to 500, preferably 10 to 200 and more preferably 15 to 100 parts per million by weight of the reaction medium. The tertiary phosphine or phosphite is suitably present in a concentration of 2 to 200 and preferably 5 to 100 moles per gram atom of rhodium. The concentration of acid is suitably $10^{-5}$ to $10^{-2}$ and preferably $10^{-4}$ to $10^{-2}$ equivalents per liter of the reaction medium over and above 1 equivalent per gram atom of rhodium. The acid is preferably present in an amount of 1.2 to 20 and preferably 1.5 to 10 equivalents of acid per gram atom of rhodium if the acid is a strong acid, for example sulphuric acid, a sulphonic acid or phosphoric or phosphorous acid. Higher concentrations of weak acids are necessary to produce an equivalent effect. For example the concentration of formic acid should be 10 times as high and acetic acid 20 times as high. It is preferred that the acid should be sulphuric acid or a sulphonic acid which is soluble in the reaction medium, for example paratoluene sulphonic acid. Among weaker acids which may be employed are the carboxylic acids having 1 to 4 carbon atoms.

A strong acid may be provided as an ester. It is preferred that the ester should be a $C_1$ to $C_4$ alkyl ester of sulphuric or a sulphonic acid which is soluble in the reaction medium. We have found that provision of the acid in this form can give selectivities to dialdehyde and unsaturated mono-aldehyde and acetals thereof higher than those of the acids themselves. It is not however known whether this is due to a catalytic activity of the esters as such or, for example, to a progressive release of free acid as the reaction proceeds. It is believed that in time an equilibrium will be established between the free acid and the ester present which will depend on the concentration of alcohol and water in the reaction medium. To this extent, the free acids and the esters are equivalents after an initial period.

By "equivalent" is meant the gram equivalent weight.

The tertiary phosphine or phosphite suitably comprises 3 to 50 for example 10 to 30 carbon atoms which may be in the form of alkyl, aryl, aralkyl or alkaryl groups. The three groups may be the same or different from one another. Very suitably tertiary phosphines, for example triaryl phosphines are used.

The process may be carried out at a temperature in the range 70° to 200° C. and preferably 100° to 170° C.

The partial pressure of carbon monoxide and hydrogen during the reaction is in each case suitably in the range 50 to 1,000 bars. Preferably the molar ratio of carbon monoxide to hydrogen is in the range 5:1 to 1:5 eg 5:1 to 1:2 and more preferably in the range 2:1 to 1:2.

The alcohol is suitably a $C_1$ to $C_4$ alcohol especially ethanol and is preferably methanol. The molar ratio of alcohol to diene is suitably in the range 3:1 to 20:1 and is preferably 5:1 to 15:1. If desired a solvent may be present.

The products of the invention in general comprise acetals of dialdehydes having 2 more carbon atoms than the conjugated diolefine with a considerable amount of branched chain isomer. Dialdehydes may be recovered from the acetal produced by hydrolysis in the presence of an acid for example acetic acid. The dialdehydes are useful as chemical intermediates and appear to be valuable as bactericides which are effective against aerobic and anaerobic bacteria. They may be used to suppress sulphate reducing bacteria which produce hydrogen sulphide in oil wells by including them in injection water, completion or workover fluids, fracturing fluids, drilling muds and/or packer fluids, or as for example components of antiseptics for use against bacteria.

EXAMPLE 1 (COMPARATIVE)

Methanol (60 ml), butadiene (15 ml), $RhH(CO)(PPh_3)_3$ (0.05 g≡0.054 millimoles≡$7.2 \times 10^{-4}$ moles/liter) and triphenylphosphine (0.75 g≡2.86 millimoles≡$3.8 \times 10^{-2}$ moles/liter) were reacted in a stirred stainless steel pressure vessel in the presence of an equimolar mixture of CO and $H_2$ at 250–270 bars pressure at 120° C. After 5 hours the concentration of $C_6$ dialdehydes was 0.26 moles/liter with 0.4 moles/liter of saturated $C_5$ monoaldehyde. Most of the butadiene had been converted to unwanted high molecular weight products.

EXAMPLE 2 (COMPARATIVE)

Methanol (60 ml), butadiene (15 ml), $RhCl(CO)(PPh_3)_2$ (0.037≡0.054 millimoles≡$7.2 \times 10^{-4}$ moles/liter) and triphenylphosphine (0.75 g) were reacted as in Example 1. After 5 hours the concentration of $C_6$ dialdehydes was 1.85 moles/liter with 0.34 moles/liter of saturated $C_5$ monoaldehydes and 0.3 moles/liter of unsaturated $C_5$ monoaldehyde intermediates. This represents a selectivity of 80.0% to the required dialdehydes.

EXAMPLE 3

Example 1 was repeated but with the addition of p-toluenesulphonic acid (0.015 g≡0.080 millimoles≡$1.05 \times 10^{-3}$ moles/liter) giving a ratio of equivalents of acid to gram atoms of rhodium of 1.5. After 5 hours the concentration of $C_6$ dialdehydes was 2.4 moles/liter with 0.4 moles/liter of saturated $C_5$ monoaldehyde and 0.1 moles/liter of unsaturated $C_5$ monoaldehyde intermediates. This represents a selectivity of 82.8% to the required dialdehydes.

EXAMPLE 4

Example 1 was repeated but adding sulphuric acid (0.054 millimoles). The ratio of equivalents of acid to gram atoms of rhodium was 2.0. After 5 hours $C_6$ dialdehyde concentration was 2.18 moles/liter with 0.34 moles/liter of $C_5$ saturated monoaldehyde and 0.06 moles/liter of $C_5$ unsaturated monoaldehyde intermediate. This represents a selectivity to the required dialdehydes of 85.0%.

EXAMPLE 5

This example shows that intermediate unsaturated $C_5$ monoaldehydes can be produced as the main product. Example 3 was repeated at 90° C. After 5 hours the concentration of $C_6$ dialdehydes was 0.35 moles/liter with 1.55 moles/liter of unsaturated $C_5$ monoaldehydes and 0.15 moles/liter of saturated $C_5$ monoaldehydes. Selectivity to unsaturated $C_5$ monoaldehyde=75.6%.

EXAMPLE 6

Methanol (60 ml), butadiene (15 ml), Rh as stearate (0.054 millimoles$\equiv 7.2\times 10^{-4}$ moles/liter Rh$\simeq$75 mg/liter, p-toluenesulphonic acid (30 mg$\equiv$0.16 millimoles$\equiv 1.12\times 10^{-3}$ moles/liter representing 1.5 equivalents of excess acid per gram atom of rhodium) and triphenylphosphine (0.75 g) were reacted as in Example 1 at 120° C. After 5 hours the concentration of $C_6$ dialdehydes was 1.5 moles/liter with 0.04 moles/liter of unsaturated $C_5$ monoaldehyde intermediates and 0.22 moles/liter of saturated $C_5$ monoaldehydes. This represents a selectivity to dialdehyde of 85.0%.

EXAMPLE 7 (COMPARATIVE)

Methanol (60 ml), butadiene (15 ml), (RhH(CO)(PPh$_3$)$_3$ $3.6\times 10^{-4}$ moles/liter (0.025 g$\equiv$0.027 millimiles) and triphenylphosphine (0.375 g$\equiv$1.43 millimoles) were charged to a glass liner and pressurised with 250-270 atmospheres 1:1 CO:H$_2$ at 120° C. in a rocking autoclave. After 3 hours the autoclave was cooled, depressurised and the products analysed. The concentration of $C_6$ dialdehydes in the product was 0.59 moles/liter with 0.65 moles/liter of saturated $C_5$ monoaldehydes. A large part of the butadiene had been converted to unwanted high molecular weight products.

EXAMPLE 8 (COMPARATIVE)

Example 7 was repeated but using RhCl(CO)(PPh$_3$)$_2$ (0.0187 g$\equiv$0.027 millimoles) in place of the hydride complex. The concentration of $C_6$ dialdehydes was 0.79 moles/liter with 0.66 moles/liter of saturated $C_5$ monoaldehydes and 0.12 moles/liter of unsaturated $C_5$ monoaldehyde.

EXAMPLE 9

Example 8 was repeated but adding sulphuric acid (1.4 $\mu$l$\equiv$0.027 millimoles). The concentration of $C_6$ dialdehydes was 1.12 moles/liter with 0.36 moles/liter of saturated $C_5$ monoaldehydes and 0.72 moles/liter of unsaturated $C_5$ monoaldehyde.

EXAMPLE 10

Example 7 was repeated but adding sulphuric acid (1.4 $\mu$l$\equiv$0.027 moles). The concentration of $C_6$ dialdehydes was 1.33 moles/liter with 0.4 moles/liter of saturated $C_5$ monoaldehydes and 0.6 moles/liter of unsaturated $C_5$ monoaldehydes.

EXAMPLE 11

Example 7 was repeated but adding acetic acid (56 $\mu$l$\equiv$0.486 millimoles). The concentration of $C_6$ dialdehydes in the product was 1.8 moles/liter with 0.41 moles/liter of saturated $C_5$ monoaldehydes and 0.21 moles/liter of unsaturated $C_5$ monoaldehydes.

EXAMPLE 12

Example 7 was repeated but adding a commercially available strong acid ion exchange resin in its acidic form (Amberlyst 15). The concentration of $C_6$ dialdehydes was 1.25 moles/liter with 0.4 m/l of saturated $C_5$ monoaldehydes and 0.31 moles/liter of unsaturated $C_5$ monoaldehydes.

EXAMPLE 13

Example 7 was repeated but adding phosphoric acid (1.5 $\mu$l$\equiv$0.081 molar equivalents). The concentrations of $C_6$ dialdehydes was 1.16 moles/liter with 0.66 moles/liter of saturated $C_5$ monoaldehyde and negligible unsaturated intermediate.

EXAMPLE 14

Methanol (290 ml), butadiene (47.2 g, 72.6 ml), RhHCO(PPh$_3$)$_3$ (0.120 g), triphenyl phosphine (3.60 g) and methyl paratoluene sulphonate (0.0705 g) were charged to a stainless steel autoclave and pressurised with 250 to 270 atmospheres of an equimolar mixture of carbon monoxide and hydrogen at a temperature of 130° C. During the course of the reaction samples were taken and analysed the results being shown in the following table.

TABLE

| Sample at specified time | Valeraldehyde (I) mol/l$^{-1}$ | Valeraldehyde acetal (II) mol/l$^{-1}$ | (I) + (II) | Unsaturated acetal (III) mol/l$^{-1}$ | Dialdehydes and acetals thereof (IV) mol/l$^{-1}$ | (III + IV) | Total Products (I + II + III + IV) mol/l$^{-1}$ |
|---|---|---|---|---|---|---|---|
| 30 mins | >0.001 | 0.049 | 0.049 | 0.332 | 0.014 | 0.346 | 0.393 |
| 1 hour | 0.004 | 0.130 | 0.134 | 0.883 | 0.061 | 0.944 | 1.078 |
| 1½ hours | 0.040 | 0.301 | 0.341 | 1.367 | 0.187 | 1.554 | 1.895 |
| 2 hours | 0.071 | 0.279 | 0.350 | 1.021 | 0.733 | 1.754 | 2.104 |
| 3 hours | 0.107 | 0.286 | 0.393 | 0.488 | 1.403 | 1.891 | 2.284 |
| 4 hours | 0.169 | 0.294 | 0.463 | 0.238 | 1.609 | 1.847 | 2.310 |
| 5 hours | 0.184 | 0.284 | 0.468 | 0.082 | 1.730 | 1.812 | 2.280 |

At the end of 5 hours the selectivity to dialdehydes and acetals and unsaturated mono-aldehyde acetals was 79.5%.

In a comparative experiments in which toluene sulphonic acid was used in the same molar amount, the total yield after 5 hours of dialdehydes and their acetals and unsaturated mono-aldehyde acetal was 1.659 moles per liter and the selectivity to these products was 75.6%.

In both cases the selectivities were based on the total products detected.

The yields quoted in the above examples were determined as follows.

The values for $C_5$ monoaldehydes, both saturated and unsaturated and their acetals were determined directly by gas liquid chromatography, and the values quoted for each class of aldehyde includes that present both as free aldehyde and as acetal.

The values for $C_6$ dialdehydes were determined after hydrolysis of their acetals by the following method.

2 ml of reaction solution were evaporated at 50 mm ambient temperature to remove MeOH. For every 0.3 g of residue were added 4 ml of $H_2O$ and 0.2 g of Amberlyst 15 H-Resin and hydrolysis was achieved by warming at 50° C. for 30 mins. A known amount of Triglyme as marker was added after hydrolysis, and the product was analysed by gas liquid chromatography.

The values quoted for dialdehydes thus also include that present originally as free aldehydes and as acetals.

When p-toluene sulphonic acid is referred to in the preceding examples it was supplied as the hydrate.

We claim:

1. In a process in which an unsaturated mono- or saturated dialdehyde or acetal thereof is produced by reacting a conjugated diolefine having 4 to 6 carbon atoms with carbon monoxide, hydrogen and an alcohol in the presence of a catalyst which comprises rhodium and a tertiary phosphine or phosphite, the improvement in which an acid selected from sulfuric acid, a sulphonic acid, phosphoric acid, phosphorous acid, a $C_1$ to $C_4$ alkyl ester of sulfuric acid or a $C_1$ to $C_4$ alkyl ester of a sulphonic acid which esters are soluble in the reaction medium is present in excess of 1 equivalent per gram atom of rhodium.

2. A process as claimed in claim 1 in which the catalyst is substantially free from halogen.

3. A process as claimed in claim 1 in which rhodium is present in a concentration of 10 to 200 parts per million by weight of the reaction medium.

4. A process as claimed in claim 1 in which the tertiary phosphine or phosphite is present in a concentration of 5 to 100 moles per gram atom of rhodium.

5. A process as claimed in claim 1 in which the concentration of acid is $10^{-4}$ to $10^{-2}$ equivalents per liter of the reaction medium over and above 1 equivalent per gram atom of rhodium.

6. A process as claimed in claim 1 in which the acid is a strong acid and is present in an amount of 1.2 to 20 equivalents of acid per gram atom of rhodium.

7. A process as claimed in claim 1 in which the acid is provided as an ester of a strong acid.

8. A process as claimed in claim 1 in which the tertiary phosphine or phosphite comprises 10 to 30 carbon atoms in the form of alkyl, aryl, aralkyl or alkaryl groups.

9. A process as claimed in claim 1 which is carried out at a temperature in the range 100° to 170° C., in which the partial pressures of carbon monoxide and hydrogen during the reaction are in the range 50 to 1,000 bars and the molar ratio of carbon monoxide to hydrogen is in the range 5:1 to 1:5 and in which the molar ratio of alochol to diene is in the range 5:1 to 15:1.

10. A process as claimed in any preceding claim in which the alcohol is a $C_1$ to $C_4$ alcohol.

* * * * *